United States Patent [19]
Boldt et al.

[11] 4,361,497
[45] Nov. 30, 1982

[54] POLYMER-BOUND CYCLOPENTADIENE METAL CARBONYL COMPOUNDS AND THEIR LIGAND SUBSTITUTION DERIVATIVES

[75] Inventors: Manfred Boldt; Giuseppe Gubitosa, both of Constance, Fed. Rep. of Germany; Hans H. Brintzinger, Hermann von Vicaristrasse 33a, D-7750 Konstanz, Fed. Rep. of Germany; Ferdinand Wild, Kreuzlingen, Switzerland

[73] Assignee: Hans H. Brintzinger, Fed. Rep. of Germany

[21] Appl. No.: 915,750

[22] Filed: Jun. 15, 1978

[30] Foreign Application Priority Data

Jun. 16, 1977 [DE] Fed. Rep. of Germany ....... 2727245

[51] Int. Cl.$^3$ .................. B01J 31/20; B01J 31/24; C07F 15/00; C08F 8/42
[52] U.S. Cl. .................. 252/426; 204/159.14; 252/428; 252/431 R; 252/431 P; 252/431 N; 260/429 R; 260/429 CY; 260/429 L; 260/429.7; 260/438.5 R; 260/439 CY; 521/31; 521/53; 525/370; 585/645; 585/646
[58] Field of Search ........... 252/431 R, 431 M, 431 P, 252/430, 428, 426; 260/429 R, 429 CY, 429 L, 429.7, 438.5 R, 439 CY; 526/19, 47.6, 48.1; 521/31, 53; 525/370; 204/159.14

[56] References Cited
U.S. PATENT DOCUMENTS

| | | | |
|---|---|---|---|
| 3,306,916 | 2/1967 | Kozikowski et al. | 260/429 R |
| 3,329,695 | 7/1967 | Wilkus et al. | 260/429 R |
| 3,361,779 | 1/1968 | Coffield et al. | 260/429 R |
| 3,709,861 | 1/1973 | Anderson | 252/431 R |
| 3,844,975 | 10/1974 | Karol | 252/431 R |
| 3,998,864 | 12/1976 | Trevillyan | 260/429 R |
| 4,062,883 | 12/1977 | Hawthorne et al. | 260/429 R |
| 4,083,803 | 4/1978 | Oswald et al. | 252/430 |
| 4,098,727 | 7/1978 | Haag et al. | 252/431 P |
| 4,173,575 | 11/1979 | Carlock | 260/604 HF |

OTHER PUBLICATIONS

J. Am. Chem. Soc.-vol. 97:8:Apr. 16, 1975, pp. 2128-2132, *"Polystyrene Attached Titanocene Species Preparation & Reactions"*-W. D. Bonds, Jr. et al.

*Primary Examiner*—P. E. Konopka
*Attorney, Agent, or Firm*—Bernard, Rothwell & Brown

[57] ABSTRACT

Polymeric catalysts containing groups of the general formula: $[-(C_5R_4)Me(CO)_xL_y]_z$, wherein $(C_5R_4)$ is a sustituted or unsubstituted cyclopentadiene group; Me is a transition metal; and L is alkyl or aryl phosphine, alkyl phosphite, nitrosyl, allyl, $SnCl_3$, halogen or hydrogen. Such groups are bound to polymeric carriers such as polystyrene-based copolymers, silica gel or silicate glass. Processes for preparing such catalysts and methods for their use are also disclosed.

28 Claims, No Drawings

POLYMER-BOUND CYCLOPENTADIENE METAL CARBONYL COMPOUNDS AND THEIR LIGAND SUBSTITUTION DERIVATIVES

The invention concerns polymer-bound cyclopentadiene metal carbonyl compounds and their ligand substitution derivatives, a method for their production and use as catalysts.

The application of polymer-bound metal carbonyl compounds and their ligand substitution derivatives as catalysts has already been established. In particular, metal-carbonyls bound by phosphine groups to a polymer carrier molecule, or their derivatives with various ligands, such as halides, additional phosphine groups, and alkyl or aryl groups, have been described in German OS No. 1,800,379; British Patent Specification No. 1,236,615; U.S. Pat. No. 3,578,609; U.S. Pat. No. 3,239,570; Canadian Patent Specification No. 72-31,992; and German Pat. Nos. 2,062,351 and 2,062,352.

These types of compounds—bound by phosphine groups to a polymer carrier—of the metals cobalt, rhodium, iridium, nickel, palladium, and platinum have been used as catalysts for hydroformylation, isomerization, cyclization, hydrogenation, acetylation, and oligomerization, where oxidic materials such as silica gel have been employed as polymer carriers, as well as macroreticular, cross-linked polystyrene [See, for example, Pittman, Evans, J. Organometal. Chem. 67, 295 (1974);
Pittman, Hanes, J. Amer. Chem. Soc. 98, 5402 (1976);
Rollman; Inorg. Chim. Acta 6, 137 (1972);
Collman, J. Amer. Chem. Soc. 94, 1789 (1972);
Piacenti et al., Chim. Ind. 49, 245 (1967);
Strukul et al., Inorg. Chim. Acta 12, 15 (1975);
Bruner, Bailar, Inorg. Chem. 12, 1465 (1973);
Arai, Kaneko, Kunugi, Chem. Lett. 1975, 265;
Kim, Rase, Ind. Eng. Chem., Prod. Res. Dev. 15, 249 (1976);
Capka et al., Tetrahedron Letters 1971, 4787; and
Takaishi et al., J. Amer. Chem. Soc. 98, 5400 (1976)].

The disadvantages of these active metal compounds, bound by phosphine groups to a polymer, are the instability of phosphine-metal bonds during catalytic reactions of this nature and the partial separation of the metal from the compound with the polymer carrier during the catalytic reaction. This results in a continuous reduction of the catalytic activity of the compounds. [See, for example, Evans et al., J. Organomet. Chem. 67, 295 (1974) and Strukul et al., J. Mol. Catal. 2, 179 (1977)]

It is an object of the present invention to create new polymer-bound metal carbonyl compounds or the corresponding ligand-substitution derivatives, which are suited as catalysts for a number of chemical-technical procedures, which catalysts do not suffer from the disadvantages of already known catalysts. In particular, the invention will create polymer-bound metal carbonyl compounds and their ligand substitution derivatives that show high selectivity during chemical-technical procedures and whose activity remains undiminished over a longer period of time.

Surprisingly, it has been found that polymer-bound cyclopentadiene metal carbonyl compounds and their ligand substitution derivatives, with a bond between the polymer carrier and the active metal ligand group formed by means of the cyclopentadiene group, are stable compounds for which separation of the metal does not occur and which provide catalysts of surprisingly high activity, even over a longer period of time.

The present invention is thus directed to polymer-bound cyclopentadiene metal carbonyl compounds and their ligand substitution derivatives, which compounds and derivatives are characterized by the fact that they contain groups of the general formula $$[-(C_5R_4)Me(CO)_xL_y]_z$$

in which

R is a hydrogen atom, a $C_{1-4}$-alkyl group, a benzene group or a diphenylmethyl group, Me is a transitional metal from the 6th, 7th, or 8th neighboring group of the periodic table, x is 1, 2, or 3, as well as 0 for compounds of metals from the 8th neighboring group of the periodic table.

L is a tri($C_{1-3}$-Alkyl) phosphine group, a triphenylphosphine group, a tri($C_{1-3}$-alkyl)-phosphite group, a nitrosyl group, an allyl group, a $SnCl_3$ group, a halogen atom, or a hydrogen atom, y is 0, 1, or 2, and z is 1, 2, 3, or 4.

Such groups are covalently bound to a polymer carrier either directly or by way of methylene groups, Di($C_{1-3}$-alkyl)-methylene groups, ($C_{1-3}$alkyl)-phenyl methylene groups, diphenyl methylene groups, ($C_{2-4}$-alkylene) groups, Di($C_{1-3}$-alkyl)-silyl groups, Di($C_{1-3}$-alkoxy)-silyl groups, diphenyl silyl groups, ($C_{1-3}$-alkyl)-chlorine-silyl groups, phenyl chlorine silyl groups, dichlorine silyl groups, or by analogous silyl groups substituted with two or three groups of the general formula $-(C_5R_4)Me(CO)_xL_y$.

Thus the present invention is also directed to both mononuclear, polymer-bound cyclopentadiene metal derivatives (z=1), as well as compounds in which a bi-tetranuclear cyclopentadiene metal compound is bound to the polymer carrier (z=2, 3, or 4). The coefficients x, y, and z take on values in a way such that the $C_5R_4$-ligands, the CO-ligands, the L-ligands, and the neighboring Me-atoms of multinuclear compounds complete the electron configuration of each Me-atom in a stable 18-electron configuration.

The subject of the invention, furthermore, is a method for synthezizing of polymer-bound cyclopentadiene metal carbonyl compounds and their ligand substitution derivatives of the type described above by means of a procedure whereby the mono- or multinuclear (and, as the case may be, ligand substituted) metal carbonyl groups can be linked with the polymer carrier by way of the cyclopentadiene groups $-C_5R_4$, which in a given case can also be substituted. The polymer-cyclopentadiene-metal linkage is effected through the reaction of a reactive carbonyl compound of metals from the 6th, 7th, or 8th neighboring groups of the periodic table, or through the reaction of a corresponding ligand substitution derivative, with the cyclopentadiene residues, which are bound to the corresponding polymer carrier either directly or by way of methylene groups, Di($C_{1-3}$alkyl)-methylene groups, ($C_{1-3}$-alkyl-phenyl-methylene groups, diphenyl-methylene groups, ($C_{1-3}$-alkylene) groups, Di($C_{1-3}$-alkyl)-silyl groups, Di($C_{1-3}$-alkoxy)-silyl groups, diphenyl silyl groups, ($C_{1-3}$-alkyl)-chlorine-silyl groups, phenyl chlorine silyl groups, dichlorine silyl groups, or by way of analogous silyl groups substituted with two or three cyclopentadiene groups. The cyclopentadiene residues (under certain circumstances cyclopentadiene in its substituted form) are involved either in their protonated form, i.e., in their neutral form, $-C_5R_4H$, or in their deprotonated form, i.e., in their anionic form $-C_5R_4^-$, and the reaction takes place in a suitable, water-free solution, with an inert gas atmosphere, at a temperature between $-80°$ C. and the boiling point of the solvent, in certain circumstances under light irradiation, during a period of from 2 hours to several days. The procedure is concluded with the isolation of the polymer-bound material.

The polymer-cyclopentadiene-metal linkage can be furthermore obtained through the reaction of a ring- or ligand-substituted cyclopentadiene metal carbonyl compound of the general formula:

(in which X is a trichlorine silyl group, a dichlorine ($C_{1-3}$-alkyl)-silyl group, a dichlorine phenyl silyl group, a chlorine-di($C_{1-3}$-alkyl)-silyl group, a chlorine diphenyl silyl group, or an analogous silyl group whose chlorine atoms are replaced by $C_{1-3}$-alkoxy groups, or an analogous chlorine silyl group substituted with two or three groups of the general formula $-(C_5R_4)Me(CO)_xL_y$, or a $C_{1-3}$-alkoxy silyl group with a carrier material that contains reactive hydroxyl groups or lithium aryl groups. The reaction takes place in a water-free, inert solvent, under an inert gas atmosphere, at a temperature between room temperature and the reflux temperature of the reactive mixture, and has a duration of from 2 hours to several days; Again, the procedure concludes with the isolation of the polymer-bound material.

In addition, the invention has as its subject the application of the cyclopentadiene metal carbonyl compounds and their ligand substitution derivatives thus obtained, as catalysts for hydroformylations, carbonylations, carboxylmethylations, hydrogenations, isomerizations, oligo- and polymerizations, as well as for oxidation reactions with carbon monoxide, methanol, olefins, and other unsaturated organic compounds.

The polymers employed as the carrier for the polymer-bound cyclopentadiene metal carbonyl compounds can include macroreticular, macroporous polystyrenes, copolymerized with 5-20% benzene. The polystyrenes in general have a pore size of 100-400 Å and a specific surface of 80-300 m²/g. They are available commercially from, e.g., Bayer, AG, Leverkusen.

As further polymer-carrier substances, macroporous, precipitated silica gels can be used. Such silica gels in general have a pore volume of approx. 1 cm³/g, a specific surface of 100-600 m²/g, and a water content of 1-5%. Silica gels of this sort are commercially available from, e.g., the firm Ventron, Danvers, Mass. USA.

As polymer-carriers, macroporous silicate glasses can also be employed, which are in use for the production of polymer-bound enzyme preparations. These silicate glasses have a mean pore diameter of approx. 200-2000 Å and a specific surface of approx. 10-120 m³/g. They are available commercially from, e.g., Corning Glass, Houghton Park, N.Y., USA.

The most essential feature of the compounds produced by the invention is a covalent linkage of the cyclopentadiene groups, or the substituted cyclopentadiene groups, with the polymer carrier substance on the one side, and with a metal carbonyl residue on the other. With the use of styrene divinylbenzene copolymers, the covalent combination with the polymer carrier can be produced most simply by way of alkylene groups, preferably by way of methylene bridges, which can also be substituted by $C_{1-3}$-alkyl groups or phenyl groups.

In the case of silica gel carriers and silicate glass carriers, the covalent connection occurs most effectually between the cyclopentadiene group and an Si-atom on or in the surface of the silica gel or silicate glass, or by way of the silyl groups, which can be substituted by $C_{1-3}$-alkyl groups, $C_{1-3}$-alkoxy groups, or phenyl groups.

In the instant cyclopentadiene metal carbonyl compounds and in their ligand substitution derivatives, R is preferably a hydrogen atom. The cyclopentadiene residue can however be replaced by one, two, three, or four substituents, as will be described in more detail hereinafter. One or two substituents are preferred. In these polymer-bound cyclopentadiene metal carbonyl compounds, and their ligand substitution derivatives, R can be, for example, a $C_{1-4}$-alkyl group, such as a methyl, ethyl, propyl, isopropyl, n-butyl, isobutyl, or tert-butyl group, or an aryl-substituted group, preferably a benzene group or a diphenyl methyl group. In the preferred compounds, either all residues R are hydrogen atoms, or three of the residues R are hydrogen atoms and one of the residues R is a methyl or tert-butyl group.

The metal moiety in the compounds of this invention can be any of the transitional metals of the 6th, 7th, or 8th neighboring groups of the periodic table, for example chromium, molybdenum, tungsten, manganese, rhenium, cobalt, rhodium, iridium, nickel, palladium, and platinum. Depending on the type and valence of the metals, x can be 1, 2, or 3; for compounds of transitional metals of the 8th neighboring group of the periodic table, x can also have a value of 0. The residue L in the compounds can be a hydrogen atom, a halogen atom, such as chlorine, bromine, or iodine, an allyl-group, or a $SnCl_3$-group. L can also be a nitrosyl group, or a phosphine group, or a comparable ligand group, for example a tri($C_{1-3}$-alkyl)-phosphite group, or a combination of these groups, through which the valence shell of the particular metal's nucleus takes on the configuration of the neighboring noble gas.

The cyclopentadiene-substituted organic or oxidic polymer carrier-substances employed in the production of the compounds of this invention are produced in a well-known manner [See, for example, Bonds et al., J. Amer. Chem. Soc. 97, 2128 (1975); Chandrasekaran et al., J. Organometal. Chem. 120, 49 (1976); Jackson et al. J. Organometal. Chem. 125, 57 (1977), all of which are incorporated herein by reference.]. Through the reaction of lithiated polystyrenes with alkyl- or aryl-substituted fulvenes, cyclopentadienyl groups can be connected, over the corresponding alkyl- or aryl-substituted methylene bridges with a polystyrene carrier. For the combination of cyclopentadiene groups with silica gel- and silicate glass-carriers, as well as with lithiated polystyrene carriers, the reaction of these carrier substances with $SiCl_4$, with alkyl trichloro silane, or a dialkyl dichlorosilane, and subsequent substitution with a cyclopentadiene anion, is particularly suited.

The cyclopentadiene derivatives bound to the appropriate carrier material are combined in their protonated, neutral form $-C_5R_4H$ at a temperature between room temperature and the reflux temperature of the reactive mixture, in an inert gas atmosphere, for a period of from 4 hours to 5 days with an appropriate metal carbonyl compound in an appropriate solvent. Thus such cyclopentadiene/polymer materials can be reacted with a 1.2 to 4-fold excess of $Fe_2(CO)_9$, in relation to the $C_5R_4H$ content, in a 0.2 to 2 molar tetrahydrofuran- or diethylether-solution; or with a 1.2 to 4-fold excess of $Co_2(CO)_8$ in a 0.2–2 molar solution in dichloromethane, or other chlorinated hydrocarbon; or with a 1.2 to 4-fold excess of $Fe(CO)_5$ in an inert solvent under light irradiation; or with $Ru(CO)_3(1.5$-cyclooctadien), or with $Ru_3(CO)_{12}$ in tetrahydrofuran, or with $Cr(CO)_3(CH_3CH)_3$, $Mo(CO)_3(CH_3CN)_3$, or $W(CO)_3(CH_3CN)_3$, or an analogous ligand-substitution product of a transitional metal-carbonyl compound in an inert solvent. The resulting polymer materials are then isolated.

Cyclopentadiene derivatives linked to the particular carrier material can first be converted by reaction with a quantity of a $C_{1-4}$-alkyl-lithium compound approximating the $-C_5R_4H$ content as closely as possible, or with a quantity of a $C_{1-4}$-alkyl-grignard compound in tetrahydorfuran- or diethyl-ether-solution (0.25–2 molar) under an inert gas atmosphere in their deprotonated, anionic form $-C_5R_4^-$. In this form, in an inert gas atmosphere at a temperature from $-80°$ C. to the reflux temperature of the solvent for a period of 2 hours to 5 days, they are allowed to react with a 1.2 to 4-fold excess of $Cr(CO)_6$, in relation to the $C_5R_4^-$-content; or of $Mo(CO)_6$, $W(CO)_6$, $Mn(CO)_5Br$, $Fe_2(CO)_9$, $Ru_3(CO)_{12}$, $Ru(CO)_3Cl_2$, $(Rh(CO_2Cl)_2$, $Ni(P(C_6H_5)_3)_2Cl_2$, $Ni(C_3H_5)Br$, $Pd(C_3H_5)Cl$; $Pd(C_3H_5)Br$, $(Pd(P(C_6H_5)_3)Cl_2)_2$, or of an analogously composed compouned of a transitional metal from the 6th, 7th, or 8th neighboring group of the periodic table, in which one or several of the CO-groups or $P(C_6H_5)_3$- groups is replaced with a tri($C_{1-3}$-alkyl)-phosphine group or with a tri($C_{1-3}$-alkyl)-phosphite group, or one or several of the halogen atoms is replaced by a $SnCl_3$ group.

The procedures described above primarily produce mononuclear polymer-bound cyclopentadiene metal-carbonyl compounds, or their ligand substitution derivatives. Mono- and multinuclear polymer-bound derivatives can be obtained through the reaction of a ring- or ligand-substituted cyclopentadiene metal carbonyl compound of the general formula

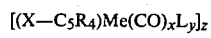
$[(X-C_5R_4)Me(CO)_xL_y]_z$

—in which X is a trichlorine silyl group, a dichlorine ($C_{1-3}$-alkyl) silyl group, a dichlorine phenyl silyl group, a chlorine-di($C_{1-3}$-alkyl) silyl group, a chlorine-diphenyl-silyl group, or an analogous silyl group, whose chlorine atoms are replaced by $C_{1-3}$-alkoxy groups, or an analogous chlorine silyl group or $C_{1-3}$-alkoxysilyl group substituted with two or three groups of the general formula $-(C_5R_4)Me(CO)_xL_y$, with a carrier material that contains reactive hydroxy groups or lithium aryl groups, in a water-free, inert solvent, in an inert-gas atmosphere at a temperature between room temperature and the reflux temperature of the reactive mixture, for a duration of from 2 hours to several days. The polymer-bound material is then isolated.

As alkoxy-silyl-substituted, or chlorine silyl-substituted, compounds of the general formula

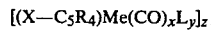
$[(X-C_5R_4)Me(CO)_xL_y]_z$ the following compounds can be used: $(X-C_5R_4)Fe(CO)_2I$, $[(X-C_5R_4)Fe(CO)_2]_2$, $[(X-C_5R_4)Fe(NO)]_2$, $[(X-C_5R_4)Fe(CO)]_4$, the analogous ruthenium compounds containing Ru instead of Fe, $(X-C_5R_4)Co(CO)_2$, $[(X-C_5R_4)Co(CO)]_2$, $[(X-C_5R_4)CoNO]_2$, $[(X-C_5R_4)Co(CO)]_3$, the analogous rhodium compounds containing Rh instead of Co, $[(X-C_5R_4)Cr(CO)_3]_2$, the corresponding molybdenum or tungsten compounds containing Mo, or W, instead of Cr, or analogously composed ligand substitution derivatives of metals from the 6th, 7th, or 8th neighboring groups of the periodic table.

For the transformation of such chlorine silyl- or alkoxy silyl-substituted components

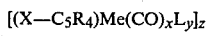
$[(X-C_5R_4)Me(CO)_xL_y]_z$ either a macroreticular, macroporous copolymer of styrene and 5–20% divinylbenzene, lithiated to have a Li-content of 0.25–1.5 mmol/g, or a macroporous silica gel, dried at 100°–800° C., or a silicate glass with a large mean pore diameter can be employed.

The compounds produced by the invention are valuable catalysts for chemical-technical procedures, particularly for the hydroformylation of olefins with CO and $H_2$, for reactions of CO with $H_2$ or methanol, but also for other reactions of unsaturated organic compounds, such as carbonylation, carboxymethylation, hydrogenation, isomerization, oligo- and polymerization reactions, as well as oxidation.

In comparison with customary catalysts the compounds produced by the invention represent a great improvement. They combine the advantages of homogenous catalysts, such as great activity and high substrate selectivity, with those of heterogenous catalysts, namely easy regenerability, simple reincorporation into the reaction, and great durability.

The following examples illustrate but do not limit the invention herein.

EXAMPLE 1

6 g of chloromethylated polystyrene (copolymerized with 18% divinylbenzene) with a chlorine content of 10.2% are brought to a swell with 80 ml of dried tetrahydrofuran for 2 hours at reflux. After cooling, the equipment is made air-free by evacuation and by filling with nitrogen. With a hypodermic needle 54 ml of 1.6 molar solution of sodium cyclopentadiene in tetrahydrofuran are then added. The mixture is boiled for 32 hours under nitrogen, then stirred for 5 days at room temperature.

The product is drawn off under protective gas, washed with tetrahydrofuran, water, and once more with tetrahydrofuran, and finally with petroleum ether, and then is dried in a vacuum. The resulting cyclopentadiene methyl polystyrene has a residual chlorine content of 2.2% and shows absorption bands typical of the $C_5H_5$ group at 1362, 895, and 820 $cm^{-1}$ in the infrared spectrum.

3.5 g of the above product is brought to a swell by stirring in 200 ml dichloroethane; under air-free conditions and with a covering atmosphere of nitrogen, 3.38 g (9.94 mmol) dicobaltoctacarbonyl are added and heated at reflux for 54.5 hours under light-free conditions. The substance is removed under nitrogen, washed with dichloromethane and petroleum ether, and dried in a vacuum. Approximately 4 g of red-brown beads, with a cobalt content of 4.3% are thus obtained. The infrared spectrum shows two absorption bands at 1955 and 2025 cm$^{-1}$, typical for polystyrene methylenecyclopentadiene cobaltdicarbonyl.

EXAMPLE 2

5 g of a polystyrene divinylbenzene polymer substituted with 1.42 meq/g $C_5H_5$—$CH_2$ following Example 1 are suspended in 60 ml tetrahydrofuran and stirred for 1 hour at room temperature. 35 ml of a 0.6 molar ethereal solution of $CH_3Li$ are then added with a hypodermic needle and stirred for 2 days at room temperature. It is then filtered and washed several times with dry tetrahydrofuran and ether, until the filtrate is neutral during hydrolysis.

The highly air-sensitive resin is suspended in 50 ml dimethylformamide. 1.6 g $Cr(CO)_6$ are added. The mixture is heated to 180° C. over 4 hours. After cooling, the mixture is filtered at room temperature and washed several times with dimethylformamide and ether until the filtrate is colorless.

The substance is left to stand for 4 hours under 2n acetic acid and then washed with nitrogen-saturated water and a mixture of water and tetrahydrofuran free of acetic acid. It is then washed with ether and dried for 2 days in a high vacuum at room temperature.

The resulting product has a chromium content of 1.55% and shows bands at 1920 and 2020 cm$^{-1}$ in the infrared spectrum typical of polystyrene methylenecylopenta/diene chromium tricarbonylhydride.

EXAMPLE 3

The analogous molybdenum and tungsten derivatives can be obtained by following the method given in Example 2, replacing $Cr(CO)_6$ with 1.88 g $Mo(CO)_6$, or with 2.5 g $W(CO)_6$, as the case may be.

The resulting products contain 4.5% Mo, or 1.65% W, and show absorption-bands at 1930 and 2030 cm$^{-1}$, or 1925 and 2020 cm$^{-1}$, in the infrared spectrum typical of polystyrene methylene cyclopentadiene molybdenum tricarbonylhydride, or polystyrol methylenecyclopentadiene tungstentricarbonyl hydride.

EXAMPLE 4

5 g of a polystyrene divinylbenzene polymer substituted with 1.42 meq./g $C_5H_5$—$CH_2$ following Example 1, are suspended under an $N_2$ atmosphere in 60 ml air-free tetrahydrofuran and stirred for 1 hour at room temperature. Then 1 g $Fe_2(CO)_9$ is added and, still under $N_2$, warmed until reflux. After 2 days it is filtered and washed several times with tetrahydrofuran until the filtrate is colorless. Following this it is washed in air-free ether and dried for 2 days at room temperature in a high vacuum.

The resulting air-sensitive product has an iron content of 2.5% and shows absorption bands at 1960 and 2040 cm$^{-1}$ in the infrared spectrum typical for polystyrene methylenecyclopentadiene ironcarbonyl hydride.

EXAMPLE 5

5 g of a polystyrene copolymerized with 18% divinylbenzene are washed with toluene and dried for 2 days at room temperature in a high vacuum.

The substance is suspended under $N_2$ in 50 ml of dry, air-free cyclohexane, and then 20 ml of 2 molar lithiumbutyl solution in hexane are added followed by 10 ml tetramethylethylene diamine. After the initially exothermic reaction subsides, the suspension is stirred for 2 days at 60° C. After cooling it is filtered at room temperature under $N_2$ and washed several times with air-free cyclohexane until the filtrate is neutral during hydrolysis.

4.5 g of the polystyrene thus lithiated are brought to a swell under $N_2$ in air-free, dry tetrahydrofurane for 1 hour at room temperature, displaced with 1.9 ml dimethylfulvene, and then stirred for 2 days at room temperature under $N_2$. It is then washed under $N_2$ with tetrahydrofuran and methanol and dried for 2 days in a high vacuum.

The resulting polystyrene dimethylene cyclopentadiene is suspended in 50 ml $CH_2Cl_2$ under a $N_2$ atmosphere and transformed with $Co_2(CO)_8$, as described in Example 1. The resulting product shows a cobalt content of 1.8% and the characteristic infrared bands at 1955 and 2025 cm$^{-1}$.

EXAMPLE 6

15 g of a macroporous silica gel (8 to 12 mesh) are dried at 600° C., degased in a vacuum, and suspended in 50 ml toluene. 3.5 ml $(C_2H_5O)_3Si(C_5H_5)$ are added and stirred 48 h at 60° C. After cooling, it is washed with chloroform and ether. The resulting product is dried for 2 days in a high vacuum at 60° C.

6.2 g of the cyclopentadiene diethoxy silyl silica gel thus obtained are suspended under a $N_2$ atmosphere in 60 ml methylenechloride and stirred after the addition of 2.9 g $Co_2(CO)_8$ for 2 days at 35° C. under $N_2$.

The mixture is then filtered in air-free conditions and washed with $CH_2Cl_2$ and ether until the filtrate is colorless. The resulting air-sensitive product is dried for 2 days in a high vacuum at room temperature. It contains 3.1% Co and shows two absorption bands at 1970 and 2025 cm$^{-1}$ typical of silica gel cyclopentadiene cobaltdicarbonyl.

EXAMPLE 7

6.2 g. of the cyclopentadiene diethoxy silyl silica gel obtained following Example 6 are held under air-free conditions with 3.2 g $Fe_2(CO)_9$ in tetrahydrofuran for 2 days at reflux temperature. After cooling, the remaining solution of the polymer material is decanted and washed with air-free tetrahydrofuran, until the remaining fluid is colorless. The polymer material is dried in a high vacuum for 2 days at room temperature. The polymer material contains 1.5% Fe and reveals infrared absorption bands at 1960 and 2030 cm$^{-1}$ typical for silica gel silyl cyclopentadiene irondicarbonylhydride.

EXAMPLE 8

6.2 g $Co_2(CO)_8$ are held in air-free conditions with 7 ml $(C_2H_5O)_3SiC_5H_5$ in methylenechloride for 12 hours at reflux temperature. After cooling, the solution is filtered, the residue washed with methylenechloride, and the combined filtrates are evaporated in a high vacuum. The remaining red oil is cooled to $-40°$ C. and decanted from the precipitated $Co_2(CO)_8$. The resulting $(C_2H_5O)_3Si(C_5H_4)Co(CO)_2$ is preserved in air-free conditions.

6 g of a coarse-grained silica gel are dried at 800° C., degased, and suspended in 30 ml toluene. Under air-free conditions, 4 ml $(C_2H_5O)_3Si(C_5H_4)Co(CO)_2$ are added, and the reactive mixture is held for 12 hours at reflux temperature. After cooling, the polymer material is isolated by decanting, washing several times with air-free toluene and air-free $CH_2Cl_2$, and subsequent drying at room temperature in a high vacuum. The resulting product contains 2.6% Co and shows the same infrared absorption bands at 1970 and 2025 cm$^{-1}$ as the material obtained in Example 6.

EXAMPLE 9

6.2 g $Co_2(CO)_8$ are transformed in the same manner as described in Example 8, with 7 ml $C_2H_2O(CH_3)_2SiC_5H_5$, to $C_2H_5O(CH_3)Si(C_5H_4)Co(CO)_2$.

6 g of coarse-grained silica gel and 4 ml $C_2H_5O(CH_3)_2Si(C_5H_4)Co(CO)_2$, once again in the same manner as described in Example 8, are converted to a dimethylsilyl cyclopentadiene cobaltdicarbonyl, which contains 1.7% Co and shows infrared absorption bands at 1970 and 2025 cm$^{-1}$ typical for this substance.

EXAMPLE 10

3.1 g $Fe(CO)_9$ are held under air-free conditions in 50 ml THF with 1.5 ml $(C_2H_5O)_3SiC_5H_5$ for 4 hours at reflux temperature. After cooling, the solvent is removed in a vacuum, the residue is taken up under a nitrogen atmosphere in petroleum ether and is filtered. After removal of the petroleum ether, $[(C_2H_5O)_3Si(C_5H_4)Fe(CO)_2]_2$ is obtained in the form of a dark red oil.

4 g of silica gel and 1.5 ml $(C_2H_5O)_3Si(C_5H_4)Fe(CO)_2$ are transformed, in the same manner described in Example 8 for $(C_2H_5O)_3Si(C_5H_4)Co(CO)_2$, into polymer-bound, binuclear ethoxy silyl cyclopentadiene irondicarbonyl dimer. The resulting material contains 1.8% Fe and shows absorption bands at 2050, 2000, 1980, 1960, and 1795 cm$^{-1}$ typical for silica gel ethoxy silyl cyclopentadiene irondicarbonyl dimer.

EXAMPLE 11

0.6 g of a polystyrene methylene cyclopentadiene cobaltdicarbonyl obtained according to Example 1 are exposed with 5 ml 1-pentene in 10 ml toluene to a CO pressure of 100 atmospheres and an $H_2$ pressure of 100 atmospheres.

Within 8 hours at 135° C. over 95% of the added pentene is converted to a mixture of n-hexanol and 2 methylpentanol. The composition of the produced mixture is given gas chromatographically as 72% n-hexanol 24% 2-methylpentanol, and 4% alcohol and other products.

EXAMPLE 12

0.5 g of a polystyrene methylene cyclopentadiene rhodiumdicarbonyl (2.5% Rh, IR bands at 1950 and 2030 cm$^{-1}$) obtained analogously to that obtained in Example 2 but with $Rh_2(CO)_4Cl_2$ instead of $Cr(CO)_6$, are exposed, as in Example 7, with 1-pentene in a toluene solution to a CO pressure of 100 atmospheres and an $H_2$ pressure of 100 atmospheres. Within 2 hours at 100° C. over 95% of the added 1-pentene is converted to a mixture of n-hexanol (approximately 62%) and 2-methylpentanol (approximately 38%).

EXAMPLE 13

2 g of a polystyrene divinylbenzene copolymer, substituted with 1.7 mmol/g —$CH_2$—$C_5H_5$ groups following Example 1, are suspended in 20 ml of petroleum ether and stirred for 1 hour at room temperature. With an hypodermic needle 7.5 ml of a 1.6 molar solution of n-butyl lithium in hexane are added and stirred at room temperature for 2 days. The resin is filtered out and washed several times with dry tetrahydrofuran, until the filtrate is neutral during hydrolysis.

To the resin suspended in 30 ml tetrahydrofuran are added 4.5 g $NiCl_2(P(C_6H_5)_3)_2$. The suspension is stirred for 4 days at room temperature and then heated for 6 hours at 40° C. After cooling, the suspension is filtered at room temperature and washed several times with tetrahydrofuran and ether, until the filtrate is colorless. The slightly red colored substance is dried for 2 days at room temperature in a high vacuum.

The product has a nickel content of 5.7%, a chlorine content of 3.6% and a phosphorus content of 3.5%, in agreement with the presence of approximately 1 mmol/g in the methylene cyclopentadiene nickel triphenylphosphine chloride (—$CH_2C_5H_4Ni(P(C_6H_5)_3)Cl$)-groups covalently bound to the polystyrene structure.

EXAMPLE 14

3 g of polystyrene divinylbenzene copolymer substituted with 1.7 mmol/g methylene cyclopentadiene (—$CH_2C_5H_5$) groups following Example 1 are suspended in tetrahydrofuran, and 14 ml of a 1.6 molar solution of n-butanol-lithium in hexane are added and stirred for 2 days at room temperature. The resin is filtered out, washed several times in dry benzene, and finally suspended in a solution of 1.8 g $Pt(CO)_2Cl_2$ in 40 ml benzene. The suspension is stirred for one day at room temperature and heated for 4 hours at 70° C. Afterward the resin is filtered out, washed several times with benzene and dried in a high vacuum.

The product thus obtained has a platinum content of 17.7% and a chlorine content of 3.2%; in the infrared spectrum it shows a strong CO band at 2050 cm$^{-1}$, corresponding to the presence of approximately 1 mmol/g in the methylenecyclopentadienplatinumcarbonyl chloride ($CH_2C_5H_4Pt(CO)Cl$) groups covalently bound to the polystyrene carrier material.

EXAMPLE 15

4 g of a polystyrene divinylbenzene copolymer, substituted with 1.7 mmol/g methylenecyclopentadiene (—$CH_2$—$C_5H_5$) groups, following Example 1, are suspended in 50 ml tetrahydrofuran and, as described in Example 2, transferred to the lithium derivative. The very air-sensitive resin is suspended in 60 ml of a 0.25 molar solution of $(NiC_3H_5Br)_2$ in benzene, stirred for 20 hours at room temperature and finally heated for ½ hour at 40° C. After cooling, it is filtered at room temperature and washed several times with tetrahydrofuran until the filtrate is colorless.

The violet resin thus obtained, substituted with methylenecyclopentadiene nickelallyl, is suspended in tetrahydrofuran and stirred for 15 hours under 30 mbar of pure NO gas at room temperature. The substance is filtered, washed several times with tetrahydrofuran, and then dried for 2 days at room temperature in a high vacuum.

The product has a nickel content of 6.2% and shows in the infrared spectrum at 1800 cm$^{-1}$ the band typical of methylenecyclopentadiene nickelnitrosyl (—$CH_2$—$C_5H_4NiNO$) substituted polystyrene.

EXAMPLE 16

6 g of a cyclopentadiene diethoethoxymethylsilyl-substituted silicagel obtained according to Example 6 are placed together with 1 g $Ru_3(CO)_{12}$ in benzene in air-free condition for 4 days at reflux temperature. After cooling, the substance is filtered out and washed several times with benzene, until the filtrate is colorless. Then it is washed twice with ether and dried for 2 days in a high vacuum.

The polymer material contains 3.7% ruthenium and shows two bands at 1970 and 2020 cm$^{-1}$ in the infrared spectrum, as is characteristic for a covalent silica gel with silycyclopentadiene rutheniumdicarbonylhydride (—Si—$C_5H_4Ru((CO)_2H)$) groups.

EXAMPLE 17

2 g of a cross-linked polystyrene, substituted with approximately 0.35 mmol/g methylenecyclopentadiene chromium tricarbonylhydride (—$CH_2$—$C_5H_4Cr(CO)_3H$) groups, obtained following Example 2, are stirred for 12 hours in 25 ml of a dioxane-water (1:1) mixture in an atmosphere of pure NO gas at room temperature. Filtering follows, and the resin is dried in a vacuum at room temperature. The product reveals IR bands at 2020 and 1945, as well as at 1705 cm$^{-1}$, as is typical for a polystyrene derivative substituted with methylenecyclopentadiene chromium dicarbonylnitrosyl (—$CH_2$—$C_5H_4Cr(CO)_2NO$) groups.

EXAMPLE 18

5.3 g of a polystyrene divinylbenzene copolymer as obtained according to Example 1, substituted with 1.8 mmol/g —$CH_2$—$C_5H_5$ groups and transferred to the lithium derivative following Example 2, are stirred at room temperature with 4.4 g $CrCl_3.3THF$ in tetrahydrofuran (THF) for 3 days. The resin is filtered out and extracted in a soxhlet's apparatus with THF for 12 hours. The blue-green material is dried in a vacuum at room temperature for 2 days. It contains 0.7 mmol/g chromium and 1.47 mmol/g chlorine, in agreement with the presence of approximately 0.7 mmol/g methylenecyclopentadiene chromic dichloride (—$CH_2$—$C_5H_4CrCl_2$) groups covalently bound to the polymer carrier material.

EXAMPLE 19

0.8 g of the polystyrene divinylbenzene copolymer obtained following Example 18, substituted with approximately 0.7 mmol/g —$CH_2$—$C_5H_4CrCl_2$ groups, are stirred in 20 ml dry tetrahydrofuran in an atmosphere of pure NO gas for 12 hours at room temperature. After filtering and drying in a vacuum at room temperature, a yellow-green material is obtained, whose content of 0.7 mmol/g chromium and 0.7 mmol/g chlorine, and whose IR-spectrum with NO-absorptions at 1700 and 1800 cm$^{-1}$ reveal that a polystyrene derivative, substituted with methylenecyclopentadiene chromic dinitrosylchloride (—$CH_2$—$C_5H_4Cr(NO)_2Cl$) groups, is present.

EXAMPLE 20

2.5 g of a polystyrene divinylbenzene copolymer as obtained following Example 18, substituted with approximately 0.35 mmol/g methylenecyclopentadiene chromic dichloride (—$CH_2C_5H_4Cl_2$) groups, are suspended under air-free conditions in 25 ml dry THF, displaced with 10 ml of a 2 molar solution of trimethylphosphite as well as with 1.0 g $LiBH_4$, and then stirred for 12 hours at room temperature. It is then filtered, and the resin is washed twice under air-free conditions, each time with 10 ml dry THF, and dried in a vacuum for 2 days at room temperature.

The product contains approximately 1.5% (0.35 mmol/g) chromium and approximately 3.0% (1.0 mmol/g) phosphorus, and represents accordingly a polystyrene derivative substituted with approximately 0.35 mmol/g methylenecyclopentadiene chromic tris(trimethylenephosphite)hydride (—$CH_2$—$C_5H_4Cr(P(OCH_3)_3)_3H$) groups.

EXAMPLE 21

1.5 g of the material obtained in Example 20 are stirred in 20 ml toluene in an atmosphere of CO-gas for 20 hours, filtered out, and dried in a vacuum at room temperature. The product now contains, with an unchanged chromium content, only 2.0% phosphorus; this and a CO-absorption at 1840 cm$^{-1}$ in the IR-spectrum demonstrate that a polystyrene derivative, with approximately 0.35 mmol/g methylenecyclopentadiene chromic bis(trimethylenephophite)carbonylhydride (—$CH_2$—$C_5H_4Cr(P(OCH_3)_3)_2(CO)H$) groups, is present.

EXAMPLE 22

1.0 g of the macroreticular polystyrene divinylbenzene copolymer, obtained following Example 20, substituted with approximately 0.35 mmol/g —$CH_2$—$C_5H_4Cr(P(OCH_3)_3)_3H$ groups, are suspended in air-free conditions in 25 mml dry THF and stirred for 12 hours at room temperature in an atmosphere of pure NO gas. Then it is filtered, and the resin is dried for 2 days in a vacuum at room temperature. A content of approxmately 1.5% chromium and approximately 2.0% phosphorus, as well as a NO-absorption at 1625 cm$^{-1}$, reveal that the product contains approximately 0.35 mmol/g methylenecyclopentadiene chromium bis(trimethylenephosphite) nitrosyl (—$CH_2$—$C_5H_4Cr(P(OCH_3)_3)_2NO$) groups covalently bound to the polymer carried material.

EXAMPLE 23

1.5 g of a macroreticular polystyrene divinylbenzene copolymer, obtained following Example 1, substituted with approximately 0.75 mmol/g —$CH_2$—$C_5H_4Co(CO)_2$ groups, are suspended under air-free conditions in 20 ml benzene, 300 mg $SnCl_4$ are added, and the mixture is stirred for 12 hours at room temperature. It is then filtered, and the resin is washed out with benzene, until the filtrate is chlorine-free, and dried for 3 days in a vacuum at room temperature.

The product shows a cobalt content of approximately 4.2% (0.72 mmol/g), a tin content of approximately 8.5% (0.73 mmol/g), and a Cl content of approximately 10% (2.8 mmol/g). This and a CO-absorption at 2080 cm$^{-1}$ in the IR-spectrum show that the product contains approximately 0.7 mmol/g methylenecyclopentadiene cobalt carbonyl trichlorostannic chloride (—$CH_2$—$C_5H_4Co(CO)(Cl)SnCl_3$) groups, covalently bound to the polymer carrier material.

EXAMPLE 24

1.8 g of a macroreticular polystyrene divinylbenzene copolymer, substituted with 0.61 mmol/g —$CH_2$—$C_5H_4W(CO)_3^-Li^+$ groups, obtained following the method given in Example 2, without, however, treating with acetic acid, are needed in THF-suspension under air-free conditions with a solution of 280 mg $SnCl_4$ in 10 ml tetrahydrofuran (THF) and stirred for 16 hours at room temperature. Then the resin is filtered out, washed several times with dry THF, until the filtrate is chloride-free, and dried in a high vacuum for 3 days at room temperature.

The product contains approximately 11% (0.6 mmol/g) tungsten, approximately 7.5% (0.62 mmol/g)

tin, and approximately 6.5% (1.84 mmol/g) chlorine. This and two CO-bands at 2045 and 1950 cm$^{-1}$ in the infrared spectrum allow the compound to be designated as a polystyrene derivative substituted with approximately 0.6 mmol/g methylenecyclopentadiene tungsten tricarbonyl stannic trichloride (—$CH_2$—$C_5H_4W$-$(CO)_3SnCl_3$) groups.

EXAMPLE 25

From a polystyrene divinylbenzene copolymer substituted with 1.8 mmol/g —$CH_2$—$C_5H_5$ groups, obtained following Example 1, 2.0 g are suspended in 50 ml tetrahydrofuran (THF), and, as described in Example 2, transferred to the lithium derivative, filtered out, and washed with toluene under air-free conditions until a neutral reaction of the filtrate occurs. The resin obtained in this manner is suspended in 30 ml toluene, cooled to approximately −70° C., and to this suspension is slowly added a solution of 650 mg bis(allylpalladiumchloride) in 15 ml toluene. This reactive mixture is first stirred for 2 hours at −70° C. and then slowly warmed while stirring to room temperature. After a further 8 hours the resin is filtered out, washed several times with toluene under air-free conditions, until the filtrate no longer contains any chloride and palladium, dried for 2 days at room temperature in a vacuum, and preserved under air-free conditions.

0.8 g of the polymer thus obtained, substituted with —$CH_2$—$C_5H_4PdC_3H_5$ groups, are suspended under air-free conditions in 15 ml toluene and stirred in an atmosphere of pure NO gas for 16 hours at room temperature. Then the resin is filtered out, washed twice with toluene, and dried for 2 days in a vacuum at room temperature.

The product contains 4.8% palladium and is designated by a NO-band at 1760 cm$^{-1}$ in the infrared spectrum as a polystyrene derivative, substituted with 0.45 mmol/g methylenecyclopentadiene palladiumnitrosyl (—$CH_2$—$C_5H_4PdNO$) groups.

EXAMPLE 26

25 g of a macroporous polystyrene divinylbenzene copolymer are stirred into 100 ml nitrobenzene for 16 hours. Then a solution of 3.6 ml acetylchloride and 6.7 g aluminium trichloride is added to 80 ml nitrobenzene, stirred 3 hours at 55° C. and then a further 3 hours at room temperature. The resin is filtered out, stirred over night in a 1:1 mixture of methanol and dioxane, then washed several times in this mixture until the filtrate is free of chloride, and dried for 3 days at room temperature in a vacuum. The product is a polystyrene derivative substituted with approximately 1.5 mmol/g $CH_3CO$ groups.

This resin is added under air-free conditions to a solution of 130 mmol cyclopentadiene-magnesiumbromide in 100 ml toluene, stirred slowly for 8 hours at 105° C., and left standing for a further 15 hours at room temperature. To form a reactive mixture, a solution of 10 g $NH_4Cl$ in 50 ml dioxane and 40 ml water, cooled with ice, is added in drops and stirred for 45 minutes. After adding a mixture of 20 ml aqueous, 32% hydrochloric acid and 50 ml dioxane, 4 further hours of stirring at room temperature follow. The mixture is then filtered, and the resin is washed first with a 1 molar aqueous hydrochloric acid, then with a 1:1 mixture of dioxane and water until the filtrate is free of chloride, and finally 3 more times with tetrahydrofuran. The product, a polystyrene derivative substituted with 1-methyl-fulvenyl-1 groups, is dried for 18 hours at room temperature in a vacuum.

3 g of the resin thus obtained are suspended in 20 ml tetrahydrofuran and reacted under air-free conditions with 10 ml of a 1.6 molar solution of methyllithium in diethylether and stirred slowly at room temperature for 2 days. The product is filtered out under air-free conditions and washed with dry THF 4 times. Then 20 ml of a 2 molar solution of acetic acid in a 1:1 mixture of dioxane and water are added, and the reactive mixture is left standing for 16 hours. The product is washed several times with a 1:1 mixture of dioxane and water, until the filtrate is chloride-free, washed again with tetrahydrofuran, and dried for 3 days in a vacuum at room temperature.

2.8 g of the resin thus added, substituted with —$C(CH_3)_2C_5H_5$ groups, are suspended in 30 ml toluene, reacted under air-free conditions with 2.5 ml iron pentacarbonyl, and held for 2 days at reflux temperature. It is then filtered, and the resin is washed with toluene under air-free conditions until the filtrate is colorless, and is dried for 2 days in a vacuum at room temperature. The product contains 2.5% iron and shows the CO-bands at 2050 and 1950 cm$^{-1}$ in the infrared spectrum, which are characteristic for polystyrene substituted with —$C(CH_3)_2C_5H_4Fe(CO)_2H$.

EXAMPLE 27

5 g of the resin with acetyl groups obtained following Example 26 are further treated as in Example 26, but using t-butylcyclopentadiene magnesiumbromide instead of cyclopentadiene magnesiumbromide. The product thus obtained, which has an iron content of 1.8% and shows characteristic CO-bands at 2040 and 1945 cm$^{-1}$ in the infrared spectrum, contains dimethylmethylene-t-butylcyclopentadiene ironcarbonylhydride (—$C(CH_3)_2C_5H_3(C_4H_9)Fe(CO_2H)$) groups covalently bound to the polymer carrier material.

EXAMPLE 28

3 g of the polystyrene divinylbenzene copolymer, substituted with 1-methyl-fulvenyl-1 groups, obtained following Example 26 are suspended in 10 ml tetrahydrofuran. Under air-free conditions a solution of 2.2 g dicyclopentadienemagnesium in 15 ml THF is added. The reactive mixture is held for 3 days at reflux temperature. Then the resin is filtered out under air-free conditions, washed with tetrahydrofuran until the filtrate reacts neutrally, and treated with 20 ml of 2 molar solution of hydrochloric acid in a 1:1 mixture of dioxane and water. The resin is washed under air-free conditions with a 1:1 mixture of dioxane and water. The resin is washed under air-free conditions with a 1:1 mixture of dioxane and water until the filtrate is acid-free, washed 2 more times with THF, and dried for 3 days in a vacuum at room temperature.

The product is suspended in 30 ml toluene, treated under air-free conditions with 4.5 ml ironpentacarbonyl, and held for 2 days at reflux temperature. Then it is filtered, and the resin is washed under air-free conditions with toluene until the filtrate is colorless and dried for 2 days at room temperature in a vacuum. The product contains 3.8% iron and shows terminal CO-bands at 2040, 1990 and 1950 cm$^{-1}$ in the infrared spectrum, as well as bridge-CO-bands at 1780 cm$^{-1}$, as they are characteristic for binuclear —$C(CH_3)(C_5H_4Fe(CO)_2)_2$ groups covalently bound to the polymer.

EXAMPLE 29

2.5 g of compound 1 are stirred with 7 g cyclopentadienthallium, as shown in the equation,

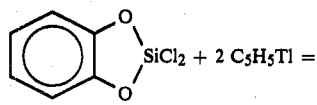 (I)

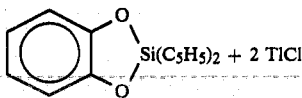

in 55 ml tetrahydrofuran at room temperature for 3 days under air-free conditions. The precipitated thallium-chloride is then filtered out and washed 2 times with 15–20 ml tetrahydrofuran. 9.5 g di-iron enneacarbonyl are added to the combined filtrate- and wash-solution. The reactive mixture is held under air-free conditions for 24 hours at reflux temperature. It is then filtered, and the filtrate is evaporated until dry.

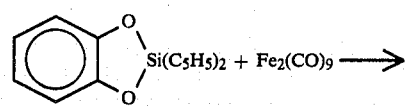 (II)

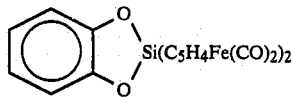

The residue, which consists of Compound II, is mixed in 75 ml toluene, 15 g of a macroporous silica gel, previously activated with sodium hydroxide, is added, and the reactive mixture is boiled under air-free conditions for 48 hours at reflux. It is then filtered, and the red-brown silica gel is extracted with toluene under air-free conditions in a soxhlet's apparatus until the eluate is colorless.

The product is dried in a vacuum for 3 days at room temperature and preserved under air-free conditions. It contains 4.8% iron and shows terminal CO-bands at 2050, 2000, and 1960 cm$^{-1}$ and bridge-CO-bands at 1775 cm$^{-1}$ in the infrared spectrum, as they are characteristic for a silica gel covalently bound with binuclear bis(cyclopentadiene irondicarbonyl) silyl (>Si(C$_5$H$_4$Fe(CO)$_2$)$_2$) groups.

EXAMPLE 30

A practically identical product as that of Example 29, with an iron content of 4.5% and with the same infrared bands, characteristic for binuclear bis(cyclopentadiene irondicarbonyl)silyl groups, is obtained when, instead of Compound II mentioned in Example 29, Compound III is used and is treated in the manner given in Example 29.

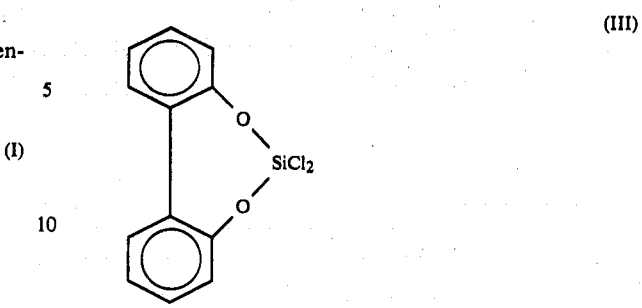 (III)

EXAMPLE 31

4 g of Compound IV are stirred with 16 g cyclopentadienethallium, corresponding to the equation

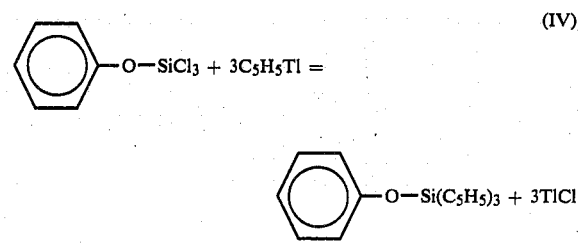 (IV)

in 80 ml tetrahydrofuran under air-free conditions for 3 days at 45° C. The precipitated thalliumchloride is then filtered out and washed 2 times with 20 ml tetrahydrofuran. The combined filtrate- and wash-solutions are evaporated in a vacuum until dry. The residue is mixed in 100 ml methylenechloride and displaced with 18.5 g dicobaltoctacarbonyl. The reactive mixture is boiled at reflux under air-free conditions for 4 days. After cooling, it is filtered and the filtrate is evaporated in a vacuum until dry. The residue is mixed in 110 ml toluene and held under air-free conditions for 2 days at reflux temperature. 15 g of a macroporous silica gel, previously activated with sodium hydroxide, is then added, and the reactive mixture is boiled for another 3 days at reflux under air-free conditions. It is then filtered. The blue-black silica gel is extracted with toluene in a soxhlet's apparatus under air-free conditions until the eluate is colorless.

The product is dried for 3 days in a vacuum at room temperature. It contains 3.7% cobalt and reveals bridge-CO-bands in the infrared spectrum at 1760 and 1670 cm$^{-1}$, as they are characteristic for a silica gel substituted with trinuclear tris(cyclopentadiene cobaltcarbonyl)silyl-(—Si(C$_5$H$_4$CoCO)$_3$) groups.

EXAMPLE 32

75 mg of polystyrene divinylbenzene copolymer substituted with 0.28 mmol/g methylenecyclopentadiene tungsten tricarbonylhydride (—CH$_2$—C$_5$H$_4$W(CO)$_3$H) groups, obtained following Example 3, are diluted under air-free conditions with 2 ml trans-3-heptene. 0.3 ml of a 0.5 molar solution of ethylaluminiumdichloride in chlorobenzene are added with a hypodermic needle, as well as 1.5 ml O$_2$ gas. The reactive mixture is stirred at room temperature. After 2 hours 0.4 ml of the reactive solution are taken out, diluted with 0.25 ml methanol and analyzed gas-chromatographically. The quantitative evaluation reveals that the reactive mixture contains 42% 3-heptene, 19% 3-hexene, and 24% 3-octene, i.e., that a metathetical olefin dismutation is catalyzed.

What is claimed is:

1. Polymer-bound cyclopentadiene metal carbonyl compounds and the ligand substitution derivatives thereof characterized in that said compounds and derivatives contain groups of the general formula $$[-(C_5R_4)Me(CO)_xL_y]_z$$

in which
R is a hydrogen atom, a $C_{1-4}$-alkyl group, a benzene group or a diphenylmethyl group,
Me is a transitional metal from the 6th, 7th, or 8th transitional group of the periodic table,
x is 1, 2, or 3,
L is a tri($C_{1-3}$-Alkyl) phosphine group, a triphenylphosphine group, a tri($C_{1-3}$-alkyl)-phosphite group, a nitrosyl group, an allyl group, a $SnCl_3$ group, a halogen atom, or a hydrogen atom,
y is 0, 1 or 2, and
z is 1, 2, 3, or 4,
wherein said groups are covalently bound to a polymer carrier by way of methylene groups, Di($C_{1-3}$-alkyl)-methylene groups, ($C_{1-3}$-alkyl)-phenyl methylene groups, diphenyl methylene groups, ($C_{2-4}$-alkylene) groups, Di($C_{1-3}$-alkyl)-silyl groups, Di($C_{1-3}$-alkoxy)-silyl groups, diphenyl silyl groups, ($C_{1-3}$-alkyl)-chlorine-silyl groups, phenyl chlorine silyl groups, dichlorine silyl groups, or by way of analogous silyl groups substituted with two or three groups of the general formula $-(C_5R_4)Me(CO)_xL_y$.

2. Polymer-bound cyclopentadiene metal carbonyl compounds, and the ligand substitution derivatives thereof, in accordance with claim 1, which contain as polymer carriers (a) macroreticular, coarse-grained polystyrenes substituted with 5–20% divinylbenzene; (b) coarse-grained precipitated silica gels with a large specific surface; or (c) silicate glasses of large mean pore diameter.

3. Polymer-bound cyclopentadiene metal carbonyl compounds and the ligand substitution derivatives thereof, in accordance with claim 2 wherein Me is selected from the group consisting of chromium, molybdenum, tungsten, manganese, rhenium, iron, ruthenium, cobalt, rhodium, iridium, nickel, palladium, and platinum.

4. Polymer-bound cyclopentadiene metal carbonyl compounds and the ligand substitution derivatives thereof in accordance with claims 1, 2, or 3 wherein the ligand group L is a tri ($C_{1-3}$-alkyl)-phosphine group, a triphenylphosphine group, a tri ($C_{1-3}$-alkyl)-phosphite group, a nitrosyl group, an allyl group, a $SnCl_3$ group, a halogen atom, or a hydrogen atom.

5. Polymer-bound cyclopentadiene metal carbonyl compounds, and the ligand substitution derivatives thereof, in accordance with claims 1, 2, or 3 wherein said compounds or derivatives contain mononuclear cyclopentadiene metal carbonyl groups or their ligand group L substitutes, corresponding to z=1; or bi-, tri-, or tetranuclear cyclopentadiene metal carbonyl groups, with reciprocal bonds between the metal atoms, or their ligand group L substitutes, corresponding to z=2, 3, or 4.

6. Polymer-bound cyclopentadiene metal carbonyl compounds, and the ligand substitution derivatives thereof, in accordance with claim 4 wherein said compounds and derivatives contain mononuclear cyclopentadiene metal carbonyl groups or their ligand group L substitutes, corresponding to z=1; or bi-, tri-, or tetranuclear cyclopentadiene metal carbonyl groups, with reciprocal bonds between the metal atoms, or their ligand group L substitutes, corresponding to z=2, 3, or 4.

7. Compounds and derivatives of claim 1, prepared by a process which comprises:
(a) reacting
 (i) a reactive metal carbonyl compound or ligand substitution derivative thereof, wherein said metal is from the 6th, 7th, or 8th transitional group of the periodic table; and
 (ii) a protonated or deprotonated cyclopentadiene residue which is bound to a polymer carrier by way of methylene groups, Di($C_{1-3}$-alkyl)-methylene groups, ($C_{1-3}$-alkyl)-phenyl-methylene groups, diphenyl methylene groups, ($C_{1-3}$-alkylene) groups, Di($C_{1-3}$-alkyl)-silyl groups, Di($C_{1-3}$-alkoxy)-silyl groups, diphenylsilyl groups, ($C_{1-3}$-alkyl)-chlorine-silyl groups, phenyl chlorine silyl groups, dichlorine silyl groups, or by way of analogous silyl groups substituted with two or three cyclopentadiene groups;
wherein the reaction occurs in a water-free solvent under an inert gas atmosphere at a temperature between $-80°$ C. and the solvent boiling point for a period of from about 2 hours to several days; followed by
(b) isolating said compound or derivative from the reaction mixture.

8. Compounds and derivatives in accordance with claim 7 wherein the reaction takes place under light irradiation.

9. Compounds and derivatives in accordance with claim 7 wherein the cyclopentadiene substituted polymer carrier is selected from the group consisting of:
(a) macroreticular, macroporous polystyrenes copolymerized with 5–20% divinylbenzene which contain cyclopentadiene residues which are unsubstituted or substituted with one or more $C_1$–$C_4$ alkyl groups, benzene groups, or diphenylmethyl groups, which residues are bound to 2–25% of the copolymer phenyl rings by way of methylene groups, Di($C_{1-3}$-alkyl)-methylene groups, ($C_{1-3}$-alkyl)-phenyl-methylene groups, diphenyl methylene groups, ($C_{2-4}$-alkylene) groups, Di($C_{1-3}$-alkyl) silyl groups, diphenyl silyl groups, or by way of analogous silyl groups which are substituted with two or three cyclopentadiene groups;
(b) macroporous, freshly precipitated silica gels which contain 0.2–0.75 mmol $C_5R_4$-groups per gram of silica gel bound to silicon atoms on or in the surface of the gel, by way of Di($C_{1-3}$-alkyl)-silyl groups, diphenyl silyl groups, Di($C_{1-3}$-alkoxy)-silyl groups, or dichlorosilyl groups, or by way of analogous silyl groups substituted with two or three cyclopentadiene groups, to terminal SiO groups in the surface of the silica gel; and
(c) silicate glass polymers with a large average pore diameter, which polymers contain 0.02–0.25 mmol $C_5R_4$-groups per gram of the silicate glass, bound to silicon atoms on or in the surface of the glass, by way of Di($C_{1-3}$-alkyl)-silyl groups, diphenyl silyl groups, Di($C_{1-3}$-alkoxy)-silyl groups, or dichlorosilyl groups, or by way of analogous silyl groups substituted with two or three cyclopentadiene groups, to terminal SiO groups in the surface of the silicate glass.

10. Compounds and derivatives in accordance with claim 9 wherein the cyclopentadiene-substituted polymer is prepared by
 (a) bringing a macroreticular, macroporous styrene/5%-20% divinylbenzene copolymer, chloromethylated to a chlorine content of 0.1-1.5 mmol per gram to a swell in tetrahydrofuran over a period of 1 to 10 hours,
 (b) adding to the copolymer/tetrahydrofuran mixture a 0.5 to 2.5 molar solution of sodium cyclopentadiene, or a substituted derivative thereof, in an amount sufficient to provide in the reaction mixture a 1.2 to 5-fold excess of the cyclopentadiene based on the copolymer chlorine content;
 (c) maintaining said reaction mixture at a temperature between room temperature and the reflux temperature of the reaction mixture for a period of from about 8 hours to 5 days under an inert atmosphere; and
 (d) isolating the resulting cyclopentadiene-substituted polymer from the reaction mixture.

11. Compounds and derivatives in accordance with claim 9 wherein the cyclopentadiene-substituted polymer is prepared by
 (a) suspending a macroreticular, macroporous styrene/5%-20% divinyl copolymer, lithiated to a lithium content of 0.25 to 1.5 mmol per gram, in tetrahydrofuran or ether solvent under an inert gas atmosphere;
 (b) adding to the copolymer/solvent mixture, a 1,1-Di($C_{1-3}$-alkyl)-fulvene, a 1-phenyl-1 ($C_{1-3}$-alkyl)-fulvene, a 1,1-diphenyl-fulvene, or a corresponding ring-substituted derivative of any of said fulvenes, in an amount sufficient to provide in the reaction mixture a 1.2 to 2.5-fold excess of the fulvene or derivative thereof based on the copolymer lithium content;
 (c) treating the reaction mixture with methanol; and
 (d) isolating the resulting cyclopentadiene-substituted polymer from the reaction mixture.

12. Compounds and derivatives in accordance with claim 9 wherein the cyclopentadiene-substituted polymer is prepared by
 (a) suspending a macroreticular, macroporous styrene/5%-20% divinyl copolymer, lithiated to a lithium content of 0.25 to 1.5 mmol per gram, in a tetrahydrofuran or diethylether solvent;
 (b) adding to the copolymer-solvent mixture a Di($C_{1-3}$-alkyl)-dichlorosilane, ($C_{1-3}$-alkyl)-trichlorosilane, or $SiCl_4$ to form a reaction mixture;
 (c) maintaining said reaction mixture at a temperature between room temperature and the reaction mixture reflux temperature for a period of from about 1 to 8 hours to form a polymer bound material;
 (d) isolating said polymer-bound material from the reaction mixture;
 (e) further reacting said polymer-bound material with a 0.5 to 2.5 molar solution of sodium cyclopentadiene or an unsubstituted derivative thereof, in an amount sufficient to provide in the reaction mixture a 1.2 to 4-fold excess of the cyclopentadiene based on the copolymer Cl content, in tetrahydrofuran, under an inert gas atmosphere, from 2 hours to 5 days, at a temperature from room temperature to reflux temperature of the reaction mixture; and
 (f) isolating the resulting cyclopentadiene-substituted polymer from the reaction mixture.

13. Compounds and derivatives in accordance with claim 9 wherein the cyclopentadiene-substituted polymer is prepared by
 (a) reacting a silica gel having a large specific surface or a silicate glass of large pore diameter with a Di ($C_{1-3}$-alkyl)-dichlorosilane, a ($C_{1-3}$-alkyl)-trichlorosilane, $SiCl_4$, or another halogen carrier to introduce SiCl groups on the surface of said silica gel or silicate glass;
 (b) drying the resulting modified silica gel or silicate glass in a high vacuum at 100° C. to 800° C. for a period of from 2 hours to 6 days;
 (c) reacting the dried modified silica gel or silicate glass with a 0.5 to 2.5 molar solution of sodium cyclopentadiene, or a substituted derivitive thereof, in an amount sufficient to provide in the reaction mixture a 1.2 to 2.5-fold excess of the cyclopentadiene, in tetrahydrofuran under an inert gas atmosphere for a period of from 5 hours to 4 days, at a temperature from room temperature to the reflux temperature of the reaction mixture; and
 (d) isolating the resulting cyclopentadiene-substituted polymer from the reaction mixture.

14. Compound and derivatives in accordance with claim 9 wherein the cyclopentadiene substituted polymer is prepared by
 (a) drying a silica gel of large specific surface or a silicate glass of large pore diameter in a high vacuum for 2 hours to 6 days at 100° C. to 800° C.;
 (b) mixing said dried silica gel or silicate glass in an inert solvent with from 0.5 to 8 mmol/g of gel or glass of a cyclopentadiene derivative selected from a ($C_{1-3}$-alkoxy)-Di ($C_{1-3}$-alkyl)-silyl-cyclopentadiene, a ($C_{1-3}$-alkoxy)-diphenyl-silyl-cyclopentadiene, a tri ($C_{1-3}$-alkoxy)-silyl-cyclopentadiene, or an analogous ($C_{1-3}$-alkoxy)-diphenyl-silyl compound substituted with two or three cyclopentadiene groups to form a reaction mixture;
 (c) maintaining said reaction mixture at a temperature from room temperature to reflux temperature of the mixture, for a period of from 4 hours to 5 days, under an inert gas atmosphere; and
 (d) isolating the resulting cyclopentadiene-substituted polymer from the reaction mixture.

15. Compounds and derivatives in accordance with claims 10, 11, 12, 13, or 14 wherein the compounds or derivatives are produced by reacting the cyclopentadiene-substituted polymers having their —$C_5R_4H$ groups in the protonated, neutral form at a temperature from room temperature to reflux temperature of the reaction mixture under an inert gas atmosphere during a period of from 4 hours to 5 days with a 1.2 to 4-fold excess of $Fe_2(CO)_9$ in a 0.2 to 2 molar tetrahydrofuran or diethylether solution; or with a 1.2 to 4-fold excess of $Co_2(CO)_8$ in a 0.2-2 molar solution in dichloromethane or similar chlorohydrocarbon; or with a 1.2 to 4-fold excess of $Fe(CO)_5$ in an inert solvent under light irradation; or with $Ru_3(CO)_{12}$ in tetrahydrofuran; or with $Ru(CO)_3$(1,5-cyclo-octadiene), $Cr(CO)_3(CH_3CN)_3$, $Mo(CO)_3(CH_3CN)_3$, or $W(CO)_3(CH_3CN)_3$, or an analogous ligand substitution product of a transitional metal in an inert solvent, and by thereafter isolating the resulting compounds or derivatives from the reaction mixture.

16. Compounds and derivatives in accordance with claims 10, 11, 12, 13, or 14 wherein the compounds or derivatives are produced by
   (a) first converting the cyclopentadiene-substituted polymers to their deprotonated anionic form by reacting said cyclopentadiene-substituted polymers with a $C_{1-4}$-alkyl-lithium compound or a $C_{1-4}$-alkyl-grignard compound in quantities approximating the $—C_5R_4H$ content of the cyclopentadiene-substituted polymers in a 0.25 to 2 molar tetrahydrofuran or diethylether solution under an inert gas atmosphere;
   (b) by secondly reacting the cyclopentadiene-substituted polymers so deprotonated with a 1.2 to 4-fold excess based on polymer $C_5R_4$ content of $Cr(CO)_6$, $Mo(CO)_6$, $W(CO)_6$, $Mn(CO)_5Br$, $Fe_2(CO)_9$, $Ru_3(CO)_{12}$, $Ru(CO)_3Cl_2$, $[Rh(CO)_2Cl]_2$, $Ni[P(C_6H_5)_3]_2Cl_2$, $Ni(C_3H_5)Br$, $Pd(C_3H_5)Cl$, $Pd(C_3H_5)Br$, $(Pd[P(C_6H_5)_3]Cl_2)_2$, or an analogously composed compound of a transitional metal from the 6th, 7th, or 8th transitional group of the periodic table in which one or more of the CO groups or $P(C_6H_5)_3$ groups is replaced by a $tri(C_{1-3}$-alkyl)-phosphine group or a $tri(C_{1-3}$-alkyl)-phosphite group or, in which one or more of the halogen atoms is replaced by a $SnCl_3$ group, under an inert gas atmosphere at a temperature from about $-80°$ C. to the reflex temperature of the reaction mixture for a period of from about 2 hours to 5 days;
   (c) by thirdly converting the anionic products so produced into the corresponding protonated compounds and derivatives by treating said anionic products with dilute, aqueous acetic acid; and
   (d) by finally isolating said compounds or derivatives from the reaction mixture.

17. Compounds and derivatives of claim 1, prepared by a process comprises
   (a) reacting
      (i) a ring- or ligand-substituted cyclopentadiene metal carbonyl compound of the general formula $[(X—C_5R_4)Me(CO)_xL_y]_z$ wherein
      R is a hydrogen atom, a $C_{1-4}$-alkyl group, a benzene group or a diphenylmethyl group; Me is a transitional metal from the 6th, 7th, or 8th transitional group of the periodic table;
      x is 1, 2, or 3;
      L is a $tri(C_{1-3}$-alkyl)-phosphine group, a triphenylphosphine group, a tri $(C_{1-3}$-alkyl)-phosphite group, a nitrosyl group, an allyl group, a $SnCl_3$ group, a halogen atom, or a hydrogen atom;
      y is 0, 1, or 2
      z is 1, 2, 3, or 4; and
      X is a trichlorine silyl group, a dichlorine $(C_{1-3}$-alkyl)-silyl group, a dichlorine phenyl silyl group, a chlorine-di($C_{1-3}$-alkyl)-silyl group, a chlorine diphenyl silyl group, or an analogous silyl group whose chlorine atoms are replaced by $C_{1-3}$-alkoxy groups, or an analogous chlorine silyl group substituted with two or three groups of the general formula $—(C_5R_4)Me(CO)_xL_y$, or a $C_{1-3}$-alkoxy-silyl group; and
      (ii) a polymeric carrier that contains reactive hydroxyl groups or lithium aryl groups; in a water-free, inert solvent, under an inert gas atmosphere, at a temperature between room temperature and the reflux temperature of the reaction mixture, for a period of 2 hours to several days; and thereafter
   (b) isolating the resulting compounds and derivatives.

18. Compounds and derivatives in accordance with claim 17 wherein the ring- or ligand-substituted cyclopentadiene metal carbonyl compound is selected from the group consisting of $(X—C_5R_4)Fe(CO_2)I$, $[(X—C_5R_4)Fe(CO)_2]_2$, $[(X—C_5R_4)Fe(NO)]_2$, $[X—C_5R_4)Fe(CO)]_4$, the analogous ruthenium compounds containing Ru instead of Fe, $(X—C_5R_4)Co(CO)_2$, $[(X—C_5R_4)Co(CO)]_2$, $[(X—C_5R_4)CoNO]_2$, $[X—C_5R_4)Co(CO)]_3$, the analogous rhodium compounds containing Rh instead of Co, $[(X—C_5R_4Cr(CO)_3]_2$, the corresponding molybdenum or tungsten compounds containing Mo or W instead of Cr, and the analoguosly composed ligand substitution derivatives of a metal from the 6th, 7th, or 8th transitional group of the periodic table.

19. Compounds and derivatives in accordance with claims 17 or 18 wherein the polymeric carrier is
   (a) a mabro-reticular, macroporous copolymer of styrene and 5-20% divinylbenzene, lithiated to a Li content of 0.25 to 1.5 mmol per gram;
   (b) a macroporous silica gel dried at $100°-800°$ C.; or
   (c) a silicate glass with large mean pore diameter.

20. A catalyst having a structure selected from the group consisting of

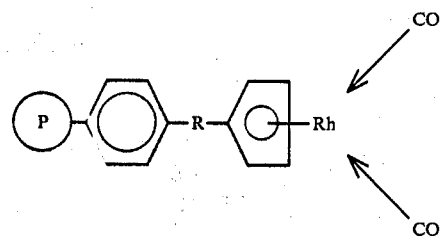

and

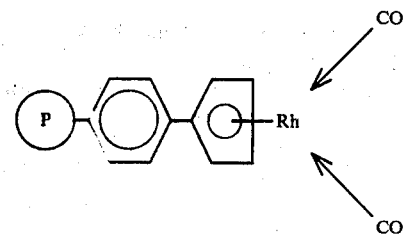

wherein R is an alkyl group containing 1 to 4 carbon atoms, and (P) represents a polystyrene polymer.

21. A catalyst as described in claim 20 wherein R is an alkyl group containing from 1 to 3 carbon atoms.

22. A method of preparing a catalyst of the formula

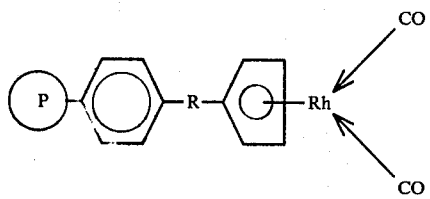

wherein R is an alkyl group containing from 1 to 4 carbon atoms and (P) is a polystyrene polymer backbone, under an inert atmosphere, comprising, (a) dissolving a compound having the structure

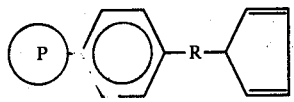

in a suitable solvent, wherein (P) and R have the meaning described above, and reacting with (b) an alkyl organolithium material containing from 1-4 carbon atoms, continuing agitation for a period of time sufficient to effect reaction;

(c) filtering the polymer from solution, readding to a suitable solvent, and adding [Rh(CO)$_2$X]$_2$ wherein X is a halogen; and (d) continuing stirring for a sufficient time to effect reaction, then removing the catalyst from solution extracting with a suitable solvent, and drying prior to use.

23. A method as described in claim 22 wherein the alkyl organolithium material is selected from the group consisting of methyl lithium, or butyl lithium.

24. A method as described in claim 23 wherein the solvents suitable for the method are selected from the group consisting of tetrahydrofuran, toluene, and dimethylformamide.

25. A method of preparing a catalyst of the formula

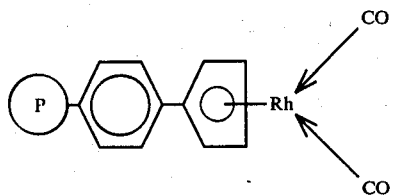

wherein (P) is a polystyrene polymer backbone, comprising, under an inert atmosphere;

(a) dissolving a polymer having the general formula;

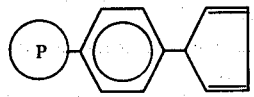

in a suitable solvent and adding an alkyl organolithium compound, stirring for sufficient time to effect reaction, filtering the polymer from solution and washing with a suitable solvent before refiltering to yield a polymer having the general formula;

(b) then adding recovered polymer to a suitable solvent and adding sufficient [Rh(CO)$_2$X]$_2$, wherein X is a halogen to provide the desired percentage of rhodium and agitating the mixture for sufficient time to effort reaction;

(c) recovering the polymer, washing with a suitable solvent, and drying to yield a polymeric catalyst having the structure;

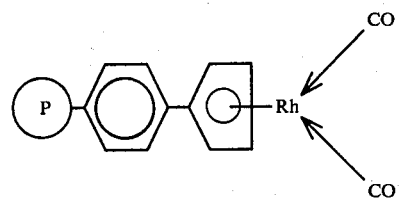

26. A method as described in claim 25 wherein the alkyl organolithium material is selected from the group consisting of methyl lithium or butyl lithium.

27. A method as described in claim 25 wherein the alkyl organolithium material contains from 1 to 4 carbon atoms.

28. A method as described in claim 25 wherein the solvents suitable for the method are selected from the group consisting of the tetrahydrofuran, toluene and dimethylformamide.

* * * * *